United States Patent
Turrigiano

(10) Patent No.: US 11,365,378 B1
(45) Date of Patent: Jun. 21, 2022

(54) DETERGENT FOR CLOTH DIAPER LAUNDRY

(71) Applicant: ESEMBLY INC., Brooklyn, NY (US)

(72) Inventor: Elizabeth Turrigiano, Brooklyn, NY (US)

(73) Assignee: ESEMBLY INC., Brooklyn, NY (US)

(*) Notice: Subject to any disclaimer, the term of this patent is extended or adjusted under 35 U.S.C. 154(b) by 0 days.

(21) Appl. No.: 16/877,478

(22) Filed: May 18, 2020

Related U.S. Application Data

(60) Provisional application No. 62/867,864, filed on Jun. 27, 2019.

(51) Int. Cl.

| C11D 11/00 | (2006.01) |
| C11D 1/72 | (2006.01) |
| A61F 13/49 | (2006.01) |
| C11D 3/00 | (2006.01) |
| C11D 3/39 | (2006.01) |
| C11D 3/04 | (2006.01) |
| C11D 3/08 | (2006.01) |
| C11D 3/10 | (2006.01) |
| C11D 3/395 | (2006.01) |

(52) U.S. Cl.
CPC .... C11D 11/0017 (2013.01); A61F 13/49003 (2013.01); C11D 1/72 (2013.01); C11D 3/001 (2013.01); C11D 3/0047 (2013.01); C11D 3/046 (2013.01); C11D 3/08 (2013.01); C11D 3/10 (2013.01); C11D 3/3942 (2013.01); C11D 3/3953 (2013.01)

(58) Field of Classification Search
CPC .................................................. C11D 11/0017
See application file for complete search history.

(56) References Cited

U.S. PATENT DOCUMENTS

| 2009/0023626 A1* | 1/2009 | Blangiforti | C11D 1/8355 510/515 |
| 2009/0035337 A1* | 2/2009 | Artiga-Gonzalez | C11D 11/0088 424/401 |
| 2011/0171155 A1* | 7/2011 | Federle | C12N 9/90 424/70.24 |
| 2013/0217608 A1* | 8/2013 | Allen | A61K 8/42 510/296 |
| 2017/0044468 A1* | 2/2017 | Gori | C12N 9/22 |

FOREIGN PATENT DOCUMENTS

WO  WO-2015166075 A1 * 11/2015 .......... C12Y 301/00

* cited by examiner

Primary Examiner — Liam J Heincer
Assistant Examiner — M. Reza Asdjodi
(74) Attorney, Agent, or Firm — Robert M Cox, Esq.

(57) ABSTRACT

A composition for a highly effective laundry detergent is disclosed specifically tailored to the needs of cleaning soiled cloth diapers without employing known skin irritants and without persistent residue accumulation. The present invention discloses a composition comprising a surface active agent, a water softener, a surface tension reducer, a bleaching agent and a pH balancing agent.

8 Claims, No Drawings

DETERGENT FOR CLOTH DIAPER LAUNDRY

FIELD OF THE INVENTION

The field of the present invention generally relates to laundry detergent formulation specifically designed for the needs of cleaning cloth diapers gently and effectively.

BACKGROUND OF THE INVENTION

Disposable diapers and baby wipes are terrible for the environment and a huge expense for new families. Babies soil 70-80 diapers per week, resulting in over 3500 disposable diapers entering our landfills by their first birthday. New parents are demanding a true planet-friendly alternative and are growing skeptical of the green-washed claims of the biodegradable disposables being marketed to them. Cloth diapers long predate our disposable culture and have seen a resurgence in popularity among frustrated eco-minded parents. Reusable diapers are truly landfill-free and enable new parents to sustainably diaper their babies.

Laundering cloth diapers is key to being able to reuse them and reduce diaper waste, and yet proper washing is the largest roadblock for new parents hesitant to embrace this diapering system. Our market currently lacks cohesive diaper laundering education AND a detergent that is powerful enough to clean a heavily soiled diaper while remaining gentle on baby skin and our planet.

A true cloth-friendly diaper detergent must be clean rinsing—meaning the formula cannot contain optical brighteners, fragrance and fabric softeners. The reason it's crucial to avoid those three ingredients is because their very purpose is to live on the surface of the fabric (after the final rinse) to perform their respective jobs (optical brighteners are multi-faceted molecules that reflect light to make fabric appear brighter, fragrance makes fabric smell nice, and fabric softeners are greasy and oily molecules that make fabric feel softer). When laundering cloth diapers, any molecule left behind is problematic because it gives the ammonia and bacteria in human waste something to bind to, making a thorough cleaning increasingly difficult with each wash. After a few weeks of using a detergent containing those ingredients, parents are left with diapers that smell horrid, repel moisture, and can even cause diaper rash. As you can imagine, the trifecta of stink, leaks and inflamed skin will lead even the most eco-minded person to throw in the towel and switch to disposable diapers. In order to create a highly effective detergent formulation excluding fragrance, fabric softeners, and optical brighteners, years of research and experimentation were necessary.

Detergents omitting both fragrance and fabric softeners (marketed as "free & clear") are known in the art; however, existing detergent formulas that exclude all 3 (fragrance, fabric softeners and optical brighteners) are only very mild "eco-friendly" detergents. These existing triple-free detergents are ineffective even at cleaning regular (single- & double-layer) household fabrics and utterly useless in cleaning cloth diapers (featuring multiple absorbent fabric layers). An highly effective triple-free formula is unknown in the art.

An ideal Cloth Diaper Laundry Detergent must feature a builder (surface tension reducer) that does not cause skin irritation. The builder/surface tension reducer opens up the fibers of the fabric thereby releasing the embedded soil and allowing the surfactant to get deep down in each layer to do its job. This is especially important when cleaning diapers because their design requires them to be made of multiple layers of thick absorbent material. The soil does not remain on the surface as it does with a standard garment made of 1-2 layers of fabric. Builder/surface tension reducers are alkalis. They naturally have a very high pH and that's what enables them to "open" the fibers. Baby skin, however, has a low pH (lower than that of adult skin). The high pH of an alkali is incompatible with the low pH of baby skin and that incompatibility can cause skin irritation. Avoiding irritation requires using alkalis that allow themselves to be thoroughly rinsed away and the pH of the fabric lowered by the right surfactant blend.

Crafting a blend of surface active agents (surfactants) capable of handling the wide range of soil that dirty diapers present is equally important. A blend of different surfactants (each targeting different soil types) is needed to clean away high concentrations of urea and ammonia as well as organic solid matter (poop) which takes on many variations depending on the baby's dietary stage and health. There are also supplements and medications that the baby is either taking directly or absorbing from infant formula or a nursing mother's breast milk. Finally (quite possibly the biggest challenge) are skincare products that parents apply on babies bottoms before diapering. Diaper creams, for example, add a tremendous amount of grease to the fabric which must be effectively removed in the wash cycle to prevent it from building up on the fabric, thereby repelling moisture. The surfactants must also break up and remove stains, suspend the soil and prevent re-deposition onto the fabric during the cycle.

Finally, being part of an eco-minded system this detergent must meet the added task of satisfying our desire to use and create products that are not environmentally hazardous. Ingredients to be chosen must score well with the EWG (environmental working group). As a result the ultimate formulation must be biodegradable, non-toxic, free of SLS, SLE, SLES, NPE, fragrances, dyes, glycols, phosphates, 1,4-dioxane, chlorine, DEA, formaldehyde, caustics, and optical brighteners.

Bottom-line, each of the selected ingredients must be highly effective at their job while also remaining gentle on sensitive baby skin.

SUMMARY OF THE INVENTION

The present invention, a cloth diaper laundry detergent, has been carefully formulated to simplify at-home cloth diaper cleaning and meet the needs of hardworking, earth-conscious families.

The ideal home-use detergent product would balance a powerful detergent formula with a completely clean rinse—remaining free of optical brighteners, fragrance and fabric softeners.

Table 1 below sets forth the ingredient functions for certain preferred ingredients of the disclosed composition.

TABLE 1

| Ingredient Function | Preferred Ingredients |
| --- | --- |
| Surface Active Agent | Alcohols, C12-15 & C12-13, Ethoxylated |
| Water Softener | Sodium Sulfate |
| Builder (Surface Tension Reducer) | Hydrous Sodium Silicate |
| Bleaching Agent (Oxidizer) | Disodium Carbonate, Compound with Hydrogen Peroxide (2:3) |
| pH Balancing Agent (Alkali) | Soda Ash Light |

First, a builder (surface tension reducer) must be selected that is highly alkaline to open up the cotton fibers and allow for deep cleaning of multi-layered cotton diapers. This builder also acts as a water softener which softens hard water by binding free water hardness ions like magnesium and calcium. Soil molecules are generally bound to the fabric surface by calcium ions. Softening of the mineral hardness in the water therefore helps with stain removal.

In one embodiment of the invention, the included builder is a hydrous sodium silicate.

In a further embodiment of the invention, a water softener (or chelating agent) is added to the formula to assist with inactivating mineral hardness. This is especially helpful for users living in areas with hard well water. This water softener further softens the water and helps to increase the efficiency of the surfactants.

In one embodiment of the invention, the water softener (or chelating agent) is a non-phosphate water softener.

In a further embodiment of the invention, the water softener (or chelating agent) is Sodium Sulfate.

In a further embodiment of the invention, one or more ionic and anionic surfactants are included in the formula.

In a further embodiment of the invention, the one or more ionic and anionic surfactants are non-sulfate surfactants.

In one embodiment of the invention, the one or more ionic and anionic surfactants are various ethoxylated alcohols.

In a further embodiment of the invention, the one or more ionic and anionic surfactants are selected from the group consisting of: Alcohols, C12-15, ethoxylated and Alcohols, C12-13, ethoxylated. For example, suitable ethoxylated alcohols could include: Tomadol 25-9, Tomadol 25-7 and Tomadol 23-5.

In a further embodiment of the invention, a bleaching agent (oxidizer) to lighten discolorations on soiled cloth diapers is included in the formula.

In one embodiment of the invention, the bleaching agent (oxidizer) is chlorine-free.

In one embodiment of the invention, the bleaching agent (oxidizer) is disodium carbonate, compound with hydrogen peroxide (2:3). For example, one suitable example of a bleaching agent (oxidizer) can be PROVOX C.

In a further embodiment of the invention, a pH balancing agent (alkali) is included in the formula.

In one embodiment of the invention the pH balancing agent (alkali) is soda ash light.

Table 2 shows minimal and preferred ranges of possible ingredients (% by weight) of a complete cloth diaper laundry detergent solution.

TABLE 2

| Ingredient (example) [Function] | Minimal Range (% by wt) | Preferred Range (% by wt) |
|---|---|---|
| Alcohols, C12-15, Ethoxylated (e.g. Tomadol 25-9) [Surface Active Agent] | 0.0% to 10.0% | 0.95% to 1.05% |
| Alcohols, C12-15, Ethoxylated (e.g. Tomadol 25-7) [Surface Active Agent] | 0.0% to 10.0% | 0.95% to 1.05% |
| Alcohols, C12-13, Ethoxylated (e.g. Tomadol 23-5) [Surface Active Agent] | 0.0% to 10.0% | 3.8% to 4.2% |
| Sodium Sulfate [Water Softener] | 10.0% to 25.0% | 17.1% to 18.9% |
| Hydrous Sodium Silicate [Surface Tension Reducer] | 0.0% to 15.0% | 9.5% to 10.5% |
| Disodium Carbonate, Compound with Hydrogen Peroxide (2:3) (e.g. PROVOX C) [Bleaching Agent] | 5.0% to 20.0% | 13.3% to 14.7% |
| Soda Ash Light [pH Balancing Agent] | 0.0% to 60.0% | 49.4% to 54.6% |

The embodiments of the invention in which an exclusive property or privilege is claimed are defined as follows:

1. A cloth diaper laundry detergent composition consisting of: (a) from [5.7]% to [6.3]% by weight of one or more surface active agents; (b) from [17.1]% to [18.9]% by weight of a water softener; (c) [from] [9.5]% to [10.5]% by weight of a surface tension reducer; (d) from [13.3]% to [14.7]% by weight of a bleaching agent; (e) from [49.4]% to [54.6]% by weight of a pH balancing agent; wherein the percentage by weight is relative to the total weight of the composition; and wherein the composition is for cleaning soiled diaper laundry.

2. The cloth diaper laundry detergent composition of claim 1, wherein the one or more surface active agents are sulfate-free, the surface tension reducer is phosphate-free, and the bleaching agent is chlorine-free.

3. The cloth diaper laundry detergent composition of claim 1, wherein the one or more surface active agents is selected from the group consisting of: alcohols, C12-15, ethoxylated and alcohols, C12-13, ethoxylated.

4. The cloth diaper laundry detergent composition of claim 1, wherein the one or more surface active agents is selected from the group consisting of: Tomadol 25-9, Tomadol 25-7 and Tomadol 23-5.

5. The cloth diaper laundry detergent of claim 1, wherein the water softener is sodium sulfate.

6. The cloth diaper laundry detergent of claim 1, wherein the surface tension reducer is hydrous sodium silicate.

7. The cloth diaper laundry detergent of claim 1, wherein the bleaching agent is sodium percarbonate.

8. The cloth diaper laundry detergent of claim 1, wherein the pH balancing agent is soda ash light.

* * * * *